(12) United States Patent
Campbell

(10) Patent No.: US 9,724,377 B1
(45) Date of Patent: Aug. 8, 2017

(54) SUPPLEMENT FOR PRODUCING CALM ALERTNESS

(71) Applicant: Slick Hunting Products Inc, Flagstaff, AZ (US)

(72) Inventor: Shawn M Campbell, Flagstaff, AZ (US)

(73) Assignee: Slick Hunting Products LLC, Flagstaff, AZ (US)

( * ) Notice: Subject to any disclaimer, the term of this patent is extended or adjusted under 35 U.S.C. 154(b) by 224 days.

(21) Appl. No.: 14/745,717

(22) Filed: Jun. 22, 2015

Related U.S. Application Data

(60) Provisional application No. 62/016,172, filed on Jun. 24, 2014.

(51) Int. Cl.
| | | |
|---|---|---|
| *A01N 65/00* | (2009.01) | |
| *A61K 36/81* | (2006.01) | |
| *A61K 36/67* | (2006.01) | |
| *A61K 36/68* | (2006.01) | |
| *A61K 36/185* | (2006.01) | |
| *A61K 36/534* | (2006.01) | |

(52) U.S. Cl.
CPC ............ *A61K 36/81* (2013.01); *A61K 36/185* (2013.01); *A61K 36/534* (2013.01); *A61K 36/67* (2013.01); *A61K 36/68* (2013.01)

(58) Field of Classification Search
CPC ...................................................... A61K 36/00
USPC ........................................................ 424/725
See application file for complete search history.

(56) References Cited

U.S. PATENT DOCUMENTS 8,377,473 B2 * 2/2013 Liu ...................... A61K 31/191
420/402

\* cited by examiner

*Primary Examiner* — Michael Meller
(74) *Attorney, Agent, or Firm* — Invention To Patent Services; Alex Hobson

(57) ABSTRACT

A supplement that produces an increased feeling of alertness and reduces anxiety, or produce a feeling of calmness is described. In an exemplary embodiment, the supplement is all natural, and contains no or essentially no synthesized chemical. The supplement or the therapeutic ingredients, such as the ingredients within a capsule, may only contain plant matter. The plant matter may include plant roots and leaves, for example. The supplement and more specifically the active ingredient of the supplement may include, *piper methysticum* (kava kava root), brahmi (*bacopa*), ashwagandha (winter cherry). These three ingredients may be the primary active or therapeutic ingredients and may be provided in an effective amount to produce a feeling of alert calmness.

1 Claim, 1 Drawing Sheet

SUPPLEMENT FOR PRODUCING CALM ALERTNESS

CROSS REFERENCE TO RELATED APPLICATIONS

This application claims the benefit of U.S. provisional patent No. 62/016,172, filed on Jun. 24, 2014 and entitled Supplement For Producing Calm Alertness.

BACKGROUND OF THE INVENTION

Field of the Invention

The present invention relates to supplements configured to increase alertness and reduce anxiety or produce a feeling of calmness and method of using said supplements.

Background

There are a wide variety of supplements available for either increasing alertness or for reducing anxiety, but there are no formulations configured to simultaneously do both. Many of the supplements directed toward increasing alertness contain ingredients that increase anxiety, such as caffeine or other stimulants. Likewise, supplements directed toward reducing anxiety typically also reduce alertness and often times contain ingredients that make a person drowsy.

There are many different situations where a person needs to be alert but also needs to remain calm. There is a need for a supplement comprising a composition to produce these two often considered disparate effects.

SUMMARY OF THE INVENTION

The invention is directed to a supplement configured to increase alertness and reduce anxiety or produce a feeling of calmness and method of using said supplements. In an exemplary embodiment, the supplement of the present invention is all-natural, and contains no, or essentially no, synthesized chemical and in a particular embodiment, no synthesized chemical as the active ingredient. The supplement, as described herein may consist essentially of plant matter including plant root and leaves, for example. In an exemplary embodiment, the entire contents of the supplement, or active ingredient, or ingredients contained within a capsule are all natural and derived directly from a plant. It is to be understood that the capsule and/or a binder in a tablet may comprise a material not derived from a plant however. The supplement, and more specifically the active ingredient of the supplement, may include *piper methysticum* (kava kava root), brahmi (*bacopa*), and ashwagandha (winter cherry). These three ingredients may be the primary active or therapeutic ingredients and may be provided in an effective amount to produce a feeling of alert calmness. The specific concentration of these ingredients may be carefully combined to produce a feeling of calm alertness. In an exemplary embodiment, the therapeutic ingredients of the supplement consists essentially of three main ingredients, *piper methysticum*, brahmi and ashwagandha. In an exemplary embodiment, any ingredient other than brahmi, present at less than 30 mg, may be considered to be a non-therapeutic ingredient or a trace ingredient as they may not have any effective therapeutic effect. In addition, any other non-therapeutic ingredients or materials such as binders or capsule material may be included in the supplement and not considered as part of the therapeutic ingredients. The supplement may further comprise any number of other ingredients, or supplemental ingredients including, but not limited to, passion flower, peppermint leaves (menthe *piperita*), vegetable cellulose and filtered water. The composition may comprise a combination of ingredients as provided in Table 1.

TABLE 1

| Ingredients | amount/mg |
|---|---|
| *Piper Methysticum* (Kava Kava Root) | 325 |
| *Brahmi* (Bacopa) | 40 |
| *Ashwagandha* (Winter Cherry) | 125 |
| Proprietary Blend Total | 490 mg |
| Other Ingredients: | |
| Passion Flower | 15-25 |
| Peppermint Leaves (*Mentha piperita*) | 15-25 |
| Vegetable Cellulose | |
| Filtered Water | |

The specific concentration of the ingredients may be varied to provide an effective amount of each ingredient. In an exemplary embodiment, the *piper methysticum* is be present in the supplement in a concentration of approximately 50% to 75% by weight of the active ingredients, the brahmi is present in a concentration of approximately 5% to 20% by weight of the active ingredients, and the ashwagandha is present in a concentration of about 15% to 40% by weight of the active ingredients. In one embodiment, the *piper methysticum* has a concentration of at least about 50%, at least about 60%, at least about 65%, at least about 75%, or any range between and including the concentrations by weight of the active ingredients provided. In one embodiment, the brahmi has a concentration by weight of the active ingredients, of at least about 2%, at least about 5%, at least about 10% or any range between and including the percentages provided. Likewise, in one embodiment, the brahmi has a concentration by weight of the active ingredients of no more than about 15%, no more than about 10%, no more than about 8%, no more than about 5% or any range between and including the concentration percentages provided. In one embodiment, the ashwagandha has a concentration by weight of the active ingredients, of at least about 15%, at least about 20%, at least about 30%, at least about 40% or any range between and including the concentration percentages provided. Likewise, in one embodiment, the ashwagandha has a concentration by weight of the active ingredients, of no more than about 40%, no more than about 35%, no more than about 25%, no more than about 20% or any range between and including the concentration percentages provided. In addition, the *piper methysticum* may consist essentially of kava kava root and comprise essentially no stems or leave of the kava kava plant.

The supplement described herein may be provided as a pill, capsule, a powder to be taken direct or with food, or prepared as a tea. In an exemplary embodiment, the ingredients are placed into a capsule and a person may take an effective number of capsules as needed, such as one, two, three, five or more than ten as needed. It is to be understood that large people may require a larger effective amount. A capsule may comprise approximately any suitable amount of the effective ingredients as listed in Table 1, such a more than about 200 mg, more than about 300 mg, more than about 400 mg, more than about 500 mg, more than about 700 mg, more than about 1000 mg or any range between and including the amounts provided.

The supplement, as described herein may be used to produce a feeling of calm alertness in an individual. There are many different situations where a person may want to have an increase feeling of calm alertness. For example, a hunter has to remain alert as they scan their surrounding for game, such as deer. When a deer comes into range and the hunter prepares to shoot, often times the hunter becomes very anxious. This condition is referred to as buck fever. Buck fever can cause the hunter to become so anxious that they cannot effectively aim and shoot, thereby missing their target. Likewise, a person engaging in any physical activity that requires a high level of alertness that also becomes anxious before the activity, may benefit from a supplement that both calms and increases alertness. Some examples of these activities are rodeo events, including bull riding, bronco riding, steer wrestling, tie-down roping, team roping, barrel racing, and the like. Other physical activities that may benefit from a supplement that produces a calm alertness include, down-hill mountain biking, mountain bike racing, motor-cross racing, automobile racing, any racing event, any team sporting event including football, basketball, soccer, rugby, lacrosse and the like. In addition, activities that produce stressful situations and require a high level of alertness may also benefit from a supplement that produce a calm alertness including, poker, chess, debates and the like. Finally, anyone preparing for a performance knows that "butterflies" are to be expected and a supplement the reduces anxiety and increases alertness would be ideal. Examples of performance activities include musical performances, presentations, theater, dance and the like.

The supplement may be taken prior to any of the activities described herein to produce a feeling of calm alertness. A person may take an effective dose prior to the event.

The summary of the invention is provided as a general introduction to some of the embodiments of the invention, and is not intended to be limiting. Additional example embodiments including variations and alternative configurations of the invention are provided herein.

BRIEF DESCRIPTION OF THE DRAWINGS

The accompanying drawings are included to provide a further understanding of the invention and are incorporated in and constitute a part of this specification, illustrate embodiments of the invention, and together with the description serve to explain the principles of the invention.

DETAILED DESCRIPTION OF THE ILLUSTRATED EMBODIMENTS

Figure 1:
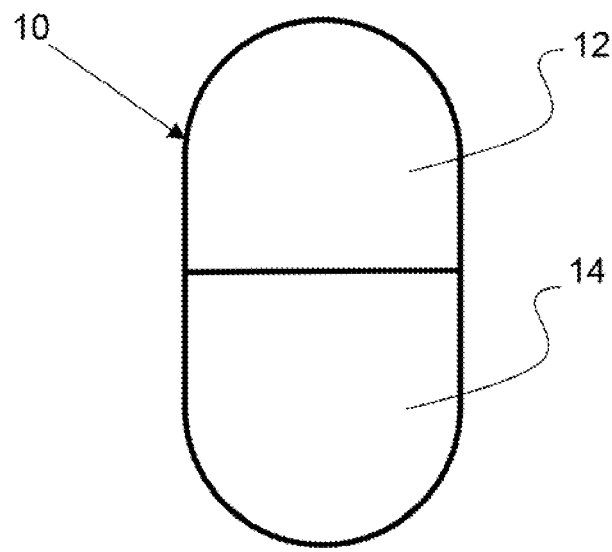
Figure 2:
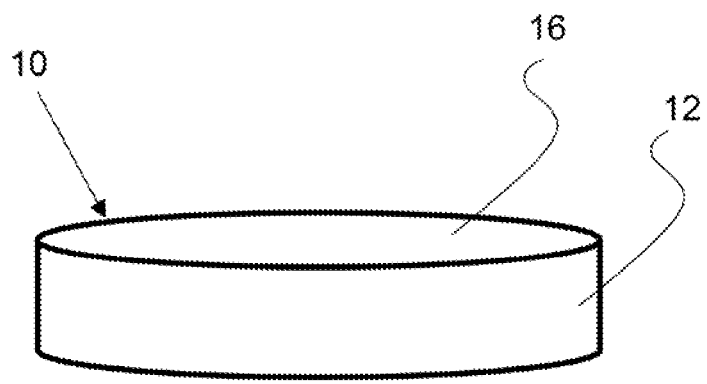

FIG. 1 shows a supplement in the form of a capsule.
FIG. 2 shows a supplement in the form of a tablet.
Corresponding reference characters indicate corresponding parts throughout the several views of the figures. The figures represent an illustration of some of the embodiments of the present invention and are not to be construed as limiting the scope of the invention in any manner. Further, the figures are not necessarily to scale, some features may be exaggerated to show details of particular components. Therefore, specific structural and functional details disclosed herein are not to be interpreted as limiting, but merely as a representative basis for teaching one skilled in the art to variously employ the present invention.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Also, use of "a" or "an" are employed to describe elements and components described herein. This is done merely for convenience and to give a general sense of the scope of the invention. This description should be read to include one or at least one and the singular also includes the plural unless it is obvious that it is meant otherwise.

Certain exemplary embodiments of the present invention are described herein and illustrated in the accompanying figures. The embodiments described are only for purposes of illustrating the present invention and should not be interpreted as limiting the scope of the invention. Other embodiments of the invention, and certain modifications, combinations and improvements of the described embodiments, will occur to those skilled in the art and all such alternate embodiments, combinations, modifications, improvements are within the scope of the present invention.

As shown if FIG. 1, the supplement 10 is in the form of a capsule 14 having the therapeutic ingredients 12 contained therein. A capsule may comprise any suitable dissolvable material and the capsule may be any suitable size. A person may take one, two, three or more capsules as desired.

As shown in FIG. 2, the supplement 10 is in the form of a tablet 16 having the therapeutic ingredients 12 contained therein. A binder may be used to form the tablet and this binder may have no therapeutic effect.

It will be apparent to those skilled in the art that various modifications, combinations and variations can be made in the present invention without departing from the spirit or scope of the invention. Specific embodiments, features and elements described herein may be modified, and/or combined in any suitable manner. Thus, it is intended that the present invention cover the modifications, combinations and variations of this invention provided they come within the scope of the appended claims and their equivalents.

What is claimed is:

1. A capsule or tablet consisting essentially of about 50%-75% of an extract of *piper methysticum*, about 15%-35% of an extract of ashwagandha and about 2%-15% of an extract of brahmi.

* * * * *